(12) United States Patent
Deisseroth

(10) Patent No.: US 10,183,067 B1
(45) Date of Patent: *Jan. 22, 2019

(54) TAA/CD4OL COMPOSITION/VACCINE FOR MALARIA

(71) Applicant: MicroVAX, LLC, Warrenton, VA (US)

(72) Inventor: Albert B. Deisseroth, Potomac, MD (US)

(73) Assignee: MicroVAX, LLC, Warrenton, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/587,777

(22) Filed: May 5, 2017

(51) Int. Cl.
*A61K 39/00* (2006.01)
*A61K 39/015* (2006.01)
*C07K 14/445* (2006.01)

(52) U.S. Cl.
CPC .......... *A61K 39/015* (2013.01); *C07K 14/445* (2013.01); *A61K 2039/53* (2013.01); *C07K 2319/02* (2013.01)

(58) Field of Classification Search
CPC .................................................. A61K 39/015
See application file for complete search history.

(56) References Cited

U.S. PATENT DOCUMENTS

| | | | | |
|---|---|---|---|---|
| 9,642,901 | B1* | 5/2017 | Deisseroth | A61K 39/015 |
| 2005/0208078 | A1* | 9/2005 | Hoffman | A61K 39/015 424/272.1 |
| 2005/0266017 | A1* | 12/2005 | Druilhe | A61K 39/015 424/191.1 |

* cited by examiner

*Primary Examiner* — Albert M Navarro
(74) *Attorney, Agent, or Firm* — Jacob Frank; Glenn Snyder

(57) ABSTRACT

Provided are compositions and methods of selecting at least three fragments one each from three domains of the malarial CSP for generating antigen specific CD8 effector T cells and non-cross reacting neutralizing antibody immune responses to the malarial parasite, which when administered prevent an infection of a human being when bitten by a malaria infected mosquito. The composition and method comprises priming an individual by administering a mixture of one or more adenoviral expression vectors encoding one or more fusion proteins, which comprises the malarial CSP antigen fragments linked to the extracellular domain of the CD40 ligand. The adenoviral expression vector comprises a transcription unit encoding a secretable fusion protein, the fusion protein containing selected malarial sporozoite CSP antigen fragments linked to the CD40 ligand to block the attachment to or infection of the human liver cell(s) by the malarial sporozoite.

11 Claims, No Drawings

Specification includes a Sequence Listing.

TAA/CD4OL COMPOSITION/VACCINE FOR MALARIA

FIELD OF THE INVENTION

The present invention relates to a composition/vaccine for the malarial sporozoite and methods of using the vaccine to develop immunity against infection by the malarial parasite.

BACKGROUND OF THE INVENTION

The following discussion of the background of the invention is merely provided to aid the reader in understanding the invention and is not admitted to describe or constitute prior art to the present invention.

Two to three hundred million infections by malarial parasites occur every year worldwide, with 1-2 million deaths per year worldwide (1-2). The fact that these deaths occur in individuals who are critically ill at the time of admission to the hospital, that over 80% of deaths occur within the first 24 hours of admission to the hospital, and that antibiotic resistant malarial parasites are spreading, mandate the development of a preventative vaccine for malaria that is more potent than existing vaccines.

Malaria Life Cycle: Infection and Intrahepatic Phase.

Infection of a human subject is initiated when the female *Anopheles* mosquito bites the human subject leading to the deposition in the blood stream of mosquito saliva which is contaminated with the infectious sporozoites. These sporozoite forms travel through the blood to the liver where they infect hepatocytes (3-4). The sporozoites replicate and mature in the hepatocytes over 8-10 days which results in the production of a large number of merozoite daughter cells which are released into the bloodstream. The malarial parasite is masked from and undetectable by the immune response while they are within the hepatocytes. The merozoite daughter cells are released from the hepatocyte by wrapping themselves in the membrane of the hepatocyte as they bud off into the blood stream. This process may mask the merozoite from detection by the immune response system.

Malaria Life Cycle: Intraerythrocytic Phase.

Once inside red cells, the merozoites increase in number and mature successively into the "ring stage", the pigmented tropozoite stage and the schizont-adhesion stage prior to red cell lysis which releases more merozoites into the blood stream. These merozoites infect more red cells and the cycle is repeated over and over again (4). This "asexual" replication phase lasts from 36-72 hours and ends in lysis of the red cell. Each cycle of replication, maturation and release requires 36 hours in *Plasmodium falciparum*, 48 hours in *P. ovale* and *P. vivax*, and 72 hours in *P. malariae*. The timing of this part of its cycle is the basis of the characteristic periodicity of the fevers and symptoms which are characteristic of malaria infections. Malarial adhesion proteins appear on the surface of the infected red cell. During this intraerythrocytic asexual replication phase, some of the merozoites develop into male and female sexual gametocytes that are taken up by the mosquito feeding on the blood. The malarial parasites are masked from the immune response while they are within the red cells.

Malaria Life Cycle: Erythrocytic Sequestration Phase.

In the case of *Plasmodium falciparum*, cell adhesion proteins are produced by the malarial parasite during the intraerythrocytic phase. One of these proteins, designated PfEMP1 (*Plasmodium falciparum* erythrocyte membrane protein, causes the infected red cells to adhere to each other, to uninfected red cells, to platelets, and to the luminal membrane of endothelial cells which line the small vessels of the body's organs (4-10). STEVOR and RIFIN are two other *plasmodium* encoded proteins which contribute to adhesion of infected red cells (11-12). The formation of these microaggregates of red cells generated by the PfEMP1 protein and other malarial adhesion proteins which appear on the infected red cell membrane then adhere to the endothelial surface, obstruct the flow of blood in the visceral microvasculature, which then leads to the symptoms of malaria: anemia, chills, fever, coma and jaundice (4). The PfEMP1 also interacts with platelets generating platelet mediated formation of red cell aggregates (5). This "sequestration" of the infected red cells as aggregates in the microvasculature, contributes to the survival of these cells since they are not subject to uptake and destruction by the reticuloendothelial cells of the liver and spleen. In addition, these red cell aggregates are responsible for the development in 1-2% of infected individuals of life-threatening consequences: thrombosis, acidosis, cerebritis, renal and hepatic failure, meningitis, pulmonary edema, and splenic rupture with hemorrhage. The aggregates of infected red cells can bind to the syncytiotrophoblast supporting the embryo during pregnancy.

Malaria Life Cycle: Replication in the Female Mosquito Salivary Glands.

The gametocytes (male and female) fertilize or fuse once in the salivary glands of the mosquito thus forming the zygote (ookinetes) which results in the development of sporozoites which are re-introduced into the blood of the next human subject who is infected.

Malaria Life Cycle: Aggregation Regulating Severity of Disease.

As stated above, only 1-2% of the infected individuals develop life threatening consequences of the sequestration. Rosetting of red cells in in vitro assays appears to correlate clinically with severity of disease. The following proteins have been shown to bind the PfEMP1 protein in the infected erythrocytes: CD36, ICAM-1, P-selectin, thrombospondin, PECAM-1/CD31, and Duffy like domains of several cellular receptors.

History of Malarial Vaccine Development by Others.

Most vaccines have attempted to use the CSP or fragments thereof, alone or attached to immunomodulatory agents, to induce an adaptive immune response in an attempt to reduce the frequency of clinically detectable malaria (13). These immunomodulatory proteins have included: the hepatitis B core antigen protein, the TLR agonist rEA, and the SLAM receptor adaptor protein EAT-2. Unfortunately, these vaccines have had limited potency (13-14). To achieve protection against malaria by CSP vaccines (the goal of which is to decrease the number of sporozoites which reach the intrahepatic phase), high titers of high affinity antibodies from long-lasting durable memory B cells are required (15).

The PfEMP1 Protein as Target for Composition/Vaccine Development.

The PfEMP1 protein, due to its exposure on the surface of the red cell membrane, and its central importance to the avoidance of destruction by the RE system, and due to the central role it plays in generating the life-threatening consequences of the disease, potentially could be an attractive target for composition/vaccine development. The difficulty in using the PfEMP1 as a target comes from the ability of the malarial parasite to switch among 60 variants of this protein, which are encoded by the "var" genes (16-17). The pathogenicity of a malarial organism can be correlated with specific forms of this gene (16-17). The development of adhesion reversing antibodies for passive administration at the time of admission of critically ill patients with malarial infections is a potentially important therapeutic approach which is under development. But treating established infections may not be as successful as prevention of the infection in the first place with vaccines.

Testing of the RTS,S Vaccine in 10 Normal Volunteers.

This vaccine, which was originally reported by Nussenzweigh (18-19), is based on the incorporation of CSP into RTS,S recombinant hybrid particles. These particles consist of a spontaneous assembly of RTS and S particles. The RTS is a fusion protein of 19 NANP CSP repeats and the hepatitis B surface antigen (HBsAg). This is co-expressed in yeast with free HBsAg, which is the S protein (20-24). This consists of amino acids 207-395 of the P. falciparum ND54/3D7 that is fused to the HBsAg protein. This approach has been shown to require adjuvants.

This vaccine induced a high level of protection against sporozoite challenge (20) in animal models. Ten normal human volunteers were vaccinated (5 with history of previous vaccinations to the hepatitis B virus and 5 without). Levels of circulating CSP specific CD8 effector T cells were thought to be important in suppressing the intrahepatic phase of the disease. It is possible that a significant portion of the immune response was against the hepatitis B surface antigen. CTLs specific for CSP peptides were not detected in these vaccines (20-25). The vaccine induced increases in the levels of RTS,S-specific CD4 T cells that released IFN-gamma within 12 hours of contract with the RTS,S-antigen. Lymphoproliferative responses were induced at low levels in a majority of test subjects. Antibody titers to the CSP NANP antigen were low even after 6 months, whereas the antibody titers to the hepatitis B surface antigen were 10 to 1000 fold higher.

Results of a Global Clinical Trial of the RTS,S Vaccine in Subjects Up to 17 Months of Age (26).

The RTS,S vaccine was given to children up to 17 months old. This generated protection in only 55% protection against acquisition of a detectable infection with malaria and 47% protection against acquisition of severe malaria. The fact that the vaccine only protected 55% of the vaccinated subjects may also reflect the low potency of the vaccine technology used (connecting the target antigen to the Hepatitis B surface core antigen).

Results of Clinical Trial of the RTS,S Vaccine in 6537 African Infants Between the Age of 6-12 Weeks Published On Line in the NEJM on Nov. 9, 2012 (27). The vaccine or a placebo was administered monthly for three administrations to 6537 African infants between the ages of 6-12 weeks along with other vaccinations. The primary endpoint of the trial was the proportion of subjects who experienced their first malarial illness during the 12 months following the third vaccination. The incidence of first malarial illnesses in the vaccine arm was 0.31/person-years and in the placebo group was 0.40/person-year for a vaccine efficacy of 30.1% (95% CI: 23.6, 36.1).

The efficacy with respect to the incidence of severe episodes of malaria was 26% in the treatment group. This result was described by the authors as a "modest" result. Despite this incomplete protection, 99.7% of the individuals who received three vaccinations, showed anti-CSP antibodies in their blood stream within 30 days of the last vaccination. The level of the antibody was 209 EU/ml. This suggests that the level of antibodies that were neutralizing in terms of infection of hepatic cells were too low for complete protection. This failed vaccine trial may also have arisen not only from the young age of the test subjects but also from the low potency of the vaccine.

Many factors can reduce the response of an individual to a viral infection or to the induction of an immune response to vaccination: chronic disease, chronic infection, cancer and advanced chronological age. Additional problems include: weak immunogenicity of the target antigen, qualitative or quantitative defects of CD4 helper T cells, defective response in the older aged population due to diminished expression of CD40L in activated CD4 helper T cells, or low levels of presentation of target antigens on Class I or II MHC in dendritic cells (DCs). Among individuals above the age of 55, less than 20% of individuals vaccinated with the yearly multi-valent particle inactivated influenza vaccine develop a fully positive immune response (28-31).

One explanation for this reduced response is the decrease in function of the immune system with age. For example, there is a decrease in the number of naïve, antigen unexposed CD4 and CD8 T cells. Additionally, the ratio of the naïve to memory CD8/CD4 cells decreases as the chronological age increases. Further, CD4 cells become impaired, acquiring both quantitative and functional defects, such as diminished levels of the CD40 ligand (CD40L) on the surface of CD4 cells as well as a temporal retardation of the rate at which CD40 ligand (CD40L) is expressed on the surface of the CD4 cells following activation. (32-33). Accordingly, the amount of antibody that an elderly system is able to generate will be lower following infection or conventional vaccination. The CD40L is important for the expansion of antigen specific CD8 effector T cells and antigen specific B cells in response to vaccination.

Development by Applicant of the TAA/ecdCD40L Vaccine Platform Which Can Overcome the Low Potency of Current Vaccine Strategies for Malaria. The vaccine strategy is based on the linkage of the target associated antigen (TAA) to the ecdCD40L. This fusion protein can be administered either as a protein, or as an expression vector carrying a transcription unit encoding the TAA/ecdCD40L (such as the Ad-sig-TAA/ecdCD40L adenoviral vector, or other viral vectors). The vaccine can also be administered as a vector prime followed in 7 and 21 days with sc injections of the TAA/ecdCD40L protein composition/vaccine. Alternatively, the vaccine can be administered as a TAA/ecdCD40L transcription unit inserted into a plasmid DNA expression vector. This vaccine was developed by the Applicant's laboratory to overcome the problems which can limit the potency and the degree of the immune response to vaccination (34-44).

Problems that Lead to Poor Response to Vaccination.

These problems include: weak immunogenicity of the target antigen, qualitative or quantitative defects of CD4 helper T cells, defective response in the older aged population due to diminished expression of CD40L in activated CD4 helper T cells, or low levels of presentation of target antigens on Class I or II MHC in dendritic cells (DCs). The CD40L is important for the expansion of antigen specific CD8 effector T cells and antigen specific B cells in response to vaccination.

TAA/ecdCD40L Composition/Vaccine Strategy of Applicant.

In order to circumvent such functional defects in the immune response, as well as increase the immunogenicity of the target associated antigens, Applicant's laboratory (34-44) designed the TAA/ecdCD40L vaccine strategy. There are four versions of this composition/vaccine: 1) One in which the TAA/ecdCD40L transcription unit is embedded in a replication incompetent adenoviral vector (Ad-sig-TAA/ecdCD40L) which is injected SC at 7 day intervals, 2) One in which the vector is used as an initial priming injection, followed by two sc injections of the TAA/ecdCD40L protein, 3) One in which the vaccine consists solely of the TAA/ecdCD40L protein which is injected 3 times at 7 day intervals, and 4) One in which the TAA/ecdCD40L is inserted into a plasmid DNA expression vector. The TAA is connected through a linker to the aminoterminal end of the ecd of the potent immunostimulatory signal CD40L.

Steps Involved in the Induction of an Immune Response by the TAA/ecdCD40L Composition/Vaccine Platform.

The attachment of fragments of the CSP (and any other TAA) to the CD40L accomplishes two things: 1) the binding of the TAA/ecdCD40L protein to the CD40 receptor on the DCs as well as on the B cells and T cells, activate these cells thereby promoting a potent immune response (34, 36, 38); 2) once the TAA/ecdCD40L protein is engaged on the CD40 receptor of the DC, the entire TAA/ecdCD40L protein is internalized into the DC in a way that allows Class I as well as Class II MHC presentation (34).

The activated TAA loaded DCs then migrate to the regional lymph nodes (41, 43) where they can activate and induce expansion of the TAA specific CD8+ effector T cells. These antigen specific CD8+ effector cells become increased in number in the lymph nodes (34, 36), egress from the lymph nodes into the peripheral blood. The antigen specific CD8 effector T cells exit the intravascular compartment and enter into the extra-vascular the sites of inflammation or infection (38). In addition to showing that this vaccine increases the antigen specific CD8+ effector T cells in the sites of inflammation (38), we have shown that the activation and expansion of the B cells by the TAA/ecdCD40L protein increases the levels of the TAA specific antibodies in the serum (38, 41-42).

SUMMARY OF THE INVENTION

Compositions/Vaccines have been described that include an adenoviral expression vector encoding a fusion protein that includes an antigen fused to CD40 ligand. See, e.g., U.S. Patent Application Publication US 2005-0226888 (application Ser. No. 11/009,533) titled "Methods for Generating Immunity to Antigen," filed Dec. 10, 2004.

The present invention provides new compositions/vaccines for protecting against infection by the malarial parasite. The TAA (of the TAA/ecdCD40L protein) for the proposed malaria composition/vaccine is the CSP protein. The CSP targets the sporozoite to the liver cell, where it mediates first the low affinity attachment, then the cleavage of the aminoterminal end, and finally, the attachment through the TSR region of the carboxyterminal end which mediates the entry of the sporozoite into the liver cell.

Proposal for Overcoming the Clinical Trial Failure to Protect All Vaccinated Individuals by Development of a TAA/ecdCD40L Preventive Malarial Vaccine Through Induction of the Adaptive Immune Response. The composition/vaccine will be directed to three regions of the CSP protein in order to block binding of the sporozoite to the liver cell and to block penetration of the sporozoite into the liver cell.

Antigen targets for composition/vaccine development include:
1. The circumsporozoite protein (CSP) is the major external antigen on the sporozoite which is present in the pre-erythrocyte phase and which infects hepatocytes;
2. The PfEMP1 protein, which is detectable on malaria infected erythrodytes.

One of the challenges to overcome with these CSP malarial proteins, is low immunogenicity. In contrast to viral infections, in which life-long immunity is conferred by a single infection, with malaria, only partial immunity is conferred even after multiple infections. The challenge with the PfEMP1 adhesion proteins is the capacity of the malarial parasite to shift among 60 variant sequences for the PfEMP1 protein, leading to an escape from the suppressive effect of the immune response on the malarial infectivity or infection. Therefore, the CSP has been chosen as the target for the composition/vaccine, rather than the PfEMP1 protein. In addition, the composition/vaccine consists of attaching fragments of the CSP protein to the ecdCD40L in order to overcome the low immunogenicity of malaria proteins.

DETAILED DESCRIPTION OF THE INVENTION

As used herein an "antigen" is any foreign material that is specifically bound by the combining site of an antibody or by the combining site of a T cell antigen receptor. Antigens may also be immunogens if they are able to trigger an immune response, or haptens if not.

As used herein, "antigenic determinant" refers to a single antigenic site or epitope on a complex antigenic molecule or particle. A minimal portion of a molecule that interacts with an antibody or T cell receptor. Antigenic determinants may be linear or discontinuous.

In one approach, the sequence encoding the malarial antigens in the fusion protein transcription unit is 5' to sequence encoding the CD40 ligand. In another approach, the sequence encoding the CD40 ligand in the fusion protein transcription unit is 5' to sequence encoding the malarial antigens. In a preferred embodiment, the CD40 ligand lacks all or a portion of its transmembrane domain.

In another aspect, the invention provides methods of immunizing an individual against infection by malaria. The method includes administering an adenoviral expression vector which includes a transcription unit encoding a secretable fusion protein that contains a CSP antigen attached to the ecdCD40 ligand. A fusion protein that encodes a CSP antigen associated with the virus and CD40 ligand may also be administered before, concurrently or after administration of the vector. Preferably, the fusion protein is administered after the vector.

In preferred embodiments, the expression vector may be a viral expression vector or a non-viral expression vector; the expression vector may be an adenoviral vector; the vector may be advantageously administered subcutaneously; the vector may be administered on a subsequent occasion(s) to increase the immune response; a signal sequence may be placed upstream of the fusion protein for secretion of the fusion protein; immunity against the antigen may be long lasting and involve generation of cytotoxic CD8+ T cells against antigen expressing cells and the production of antibody to the antigen; the transcription unit may include sequence that encodes a linker between the antigen and the CD40 ligand; suitable linkers may vary in length and composition; the expression vector may include a human cytomegalovirus promoter/enhancer for controlling transcription of the transcription unit; and the CD40 ligand may be a human CD40 ligand.

Methods to chemically couple one protein to another (carrier) protein are well known in the art and include, for example, conjugation by a water soluble carbodiimide such as 1-ethyl-3-(3dimethylaminopropyl)carbodiimide hydrochloride, conjugation by a homobifunctional cross-linker having, for example, NHS ester groups or sulfo-NHS ester analogs, conjugation by a heterobifunctional cross-linker having, for example, and NHS ester and a maleimide group such as sulfosuccinimidyl-4-(N-maleimidomethyl) cyclohexane-1-carboxylate and, conjugation with gluteraldehyde (see, for example, reference 53; see, also, U.S. Pat. Nos. 4,608,251 and 4,161,519).

The term "vector" which contains a transcription unit (aka. "expression vector") as used herein refers to viral and non-viral expression vectors that when administered in vivo can enter target cells and express an encoded protein. Viral vectors suitable for delivery in vivo and expression of an exogenous protein are well known and include adenoviral vectors, adeno-associated viral vectors, retroviral vectors, herpes simplex viral vectors, and the like. Viral vectors are preferably made replication defective in normal cells. See U.S. Pat. Nos. 6,669,942; 6,566,128; 6,794,188; 6,110,744; 6,133,029.

As used herein, the term "cells" is used expansively to encompass any living cells such as mammalian cells, plant cells, eukaryotic cells, prokaryotic cells, and the like.

The term "adenoviral expression vector" as used herein, refers to any vector from an adenovirus that includes exogenous DNA inserted into its genome which encodes a polypeptide. The vector must be capable of replicating and being packaged when any deficient essential genes are provided in trans. An adenoviral vector desirably contains at least a portion of each terminal repeat required to support the replication of the viral DNA, preferably at least about 90% of the full ITR sequence, and the DNA required to encapsidate the genome into a viral capsid. Many suitable adenoviral vectors have been described in the art. See U.S. Pat. Nos. 6,440,944 and 6,040,174 (replication defective E1 deleted vectors and specialized packaging cell lines). A preferred adenoviral expression vector is one that is replication defective in normal cells.

"Adenoviral expression vectors" may include vectors that have been modified to better target and infect specific cell types (e.g., fibroblasts and dendritic cells), or that have been modified to avoid neutralization by pre-existing, high-titer antibodies, such as the antibodies circulating in humans against Ad5 and Ad2.

Adeno-associated viruses represent a class of small, single-stranded DNA viruses that can insert their genetic material at a specific site on chromosome 19. The preparation and use of adeno-associated viral vectors for gene delivery is described in U.S. Pat. No. 5,658,785.

Non-viral vectors for gene delivery comprise various types of expression vectors (e.g., plasmids) which are combined with lipids, proteins and other molecules (or combinations of thereof) in order to protect the DNA of the vector during delivery. Fusigenic non-viral particles can be constructed by combining viral fusion proteins with expression vectors as described.

The term "transcription unit" as it is used herein in connection with an expression vector means a stretch of DNA that is transcribed as a single, continuous mRNA strand by RNA polymerase, and includes the signals for initiation and termination of transcription. For example, in one embodiment, a transcription unit of the invention includes nucleic acid that encodes from 5' to 3,' a secretory signal sequence, a malarial antigen and the ecd of the CD40 ligand. The transcription unit is in operable linkage with transcriptional and/or translational expression control elements such as a promoter and optionally any upstream or downstream enhancer element(s). A useful promoter/enhancer is the cytomegalovirus (CMV) immediate-early promoter/enhancer. See U.S. Pat. Nos. 5,849,522 and 6,218,140.

The term "secretory signal sequence" (aka. "signal sequence," "signal peptide," leader sequence," or leader peptide") as used herein refers to a short peptide sequence, generally hydrophobic in charter, including about 20 to 30 amino acids which is synthesized at the N-terminus of a polypeptide and directs the polypeptide to the endoplasmic reticulum. The secretory signal sequence is generally cleaved upon translocation of the polypeptide into the endoplasmic reticulum. Eukaryotic secretory signal sequences are preferred for directing secretion of the exogenous gene product of the expression vector. A variety of suitable such sequences are well known in the art and include the secretory signal sequence of human growth hormone, immunoglobulin kappa chain, and the like. In some embodiments, the endogenous tumor antigen signal sequence also may be used to direct secretion.

As is well known in the art, an antigen may be protein in nature, carbohydrate in nature, lipid in nature, or nucleic acid in nature, or combinations of these biomolecules. As is well known in the art, an antigen may be native, recombinant or synthetic. For example, an antigen may include non-natural molecules such as polymers and the like. Antigens include self antigens and foreign antigens such as antigens produced by another animal or antigens from an infectious agent. Infectious agent antigens may be bacterial, viral, fungal, protozoan, and the like.

In order to overcome the low immunogenicity of antigens on infectious agents like the malarial antigens used in vaccine strategies up to the present time, Applicant has formulated a new recombinant vaccine strategy which consists of attaching each of 3 "in-frame" epitopes from the circumsporozoite protein (CSP) to the aminoterminal end of the extracellular domain (ecd) of the potent immunostimulatory signal, CD40 ligand (CD40L), and administering adenoviral expression vectors carrying transcription units which encode each of these three fusion proteins subcutaneously, weekly for three administrations.

The three Malarial TAA/ecdCD40L Compositions/Vaccines. These three vaccines are as follows:

1. The Ad-sig-CSPNterRg1/ecdCD40L Vaccine. This composition/vaccine comprises an adenoviral expression vector which encodes a fusion protein comprised of (from the aminoterminal end to the carboxyterminal end): a 20 amino acid fragment (SEQ ID NO. 1 GNNEDNEKLRKP-KHKKLKQP) of region RI+ of the aminoterminal end of the CSP linked in frame to the aminoterminal end of the ecdCD40L (45). The 20 amino acid domain from the CSP is known to mediate the initial low affinity binding of the sporozoite to the heparin sulfate receptors on human hepatocytes (on the surface of liver cells) which ultimately plays a role in internalization of the sporozoite into hepatocytes. (45-47). Antibodies to this region inhibit the binding of recombinant CSP to HepG1 cells by 62% (45-47). This vaccine is called the Ad-sig-CSPNterRg1/ecdCD40L vaccine.

2. The Ad-sig-CSPRg2/ecdCD40L Composition/Vaccine. This composition/vaccine comprises an adenoviral expression vector which encodes a fusion protein comprised of (from the aminoterminal end to the carboxyterminal end): a 27 amino acid fragment (SEQ ID NO. 2 TEWS-PCSVTCGNGIQVRIKPGSANKPK) from the RII+ region of the CSP (46), which is attached in frame to the aminoterminal end of the ecdDC40L. This region is known to display a conserved amino acid sequence (to preclude immunological escape) among many isolates (45) and contributes, along with the aminoterminal region of the CSP, to the binding to heparin sulfate on the surface of the human hepatocyte (46). The vaccine is an adenoviral expression vector which encodes the following fusion protein: SEQ ID NO. 2: TEWSPCSVTCGNGIQVRIKPGSANKPK/ecdCD40L. This composition/vaccine is called the Ad-sig-CSPRg2/ecdCD40L vaccine.

3. The Ad-sig-CSPTSR/ecdCD40L Vaccine. This composition/vaccine comprises an adenoviral expression vector which encodes a fusion protein comprised of (from the aminoterminal end to the carboxyterminal end): a 23 amino acid fragment of the thrombospondin related region of CSP (also called TSR) which has the following sequence: SEQ ID NO. 3: WDEWSPCSVTCGKGTRSRKREIL (48) attached to the aminoterminal end of the ecdCD40L. This sequence is located in the carboxyterminal end of the CSP and is known to display high affinity binding to the heparin sulfate regions on human hepatocytes (3, 48-52). The vaccine is an adenoviral expression vector which encodes the following fusion protein: SEQ ID NO. 3: WDEWSPCSVTCGKGTRSRKREIL/ecdCD40L. This composition/vaccine is called the Ad-sig-CSPTSR/ecdCD40L vaccine.

The strategy here is to select multiple fragments of the CSP based on the following criteria:

1. The aminoterminal end of the CSP binds to the heparin sulfate proteoglycans on liver hepatocytes in the initial targeting and contact of the sporozoite with the target hepatic cell (see references 45-47). This region is called region R1+. In this region, there is an epitope within the aminoterminal end of CSP which interacts with the heparin sulfates on the liver cell (45-47). Selection of the fragment from this region for attachment to the ecdCD40L will be based on a size of the antigen fragment chosen should be such so as to be small enough so that it does not disrupt assembly of the CD40L homotrimer, and the presence of the heparin sulfate binding regions, and epitopes that bind to Class I and II MHC.

2. We also propose targeting sequences in the CSP which are the same in all strains (such as the RII+ region cited in references 46 and 53). The criteria for selecting sequences from the RII+ region for attachment to the ecdCD40L to create the TAA/ecdCD40L fusion protein are based on:

a. Stability of the sequences among various isolates in Region RII+;

b. Epitopes capable of binding to both class I and II MHC in order to generate both a cellular and humoral immune response to the RII+;

c. Size of the antigen fragment chosen should be such so as to be small enough so that it does not disrupt assembly of the CD40L homotrimer.

3. The "cell adhesive c-terminal region" of the CSP, the type I Thrombospondin repeat (TSR), is described in references 11 and 23. Sequences within the TSR region bind to hepatocytes with high affinity. This is known as the RIII+ region.

4. Prior to the binding of the CSP to the liver cell, the TSR RIII+ region is masked by binding to the aminoterminal third of the CSR (RI+), which itself is responsible for low affinity interactions with the liver cells that mediates the initial targeting to the liver. The interaction of the TSR region with the aminoterminal third of the CSP region defines two conformal and functional states of the CSP protein: the adhesive form, in which the aminoterminus of the CSP is not binding to the TSR (which is on the carboxyterminus of the CSP), and the migratory form in which the TSR is masked by the aminoterminus of the CSP thereby preventing the binding of the sporozoite to the cell surface. Cleavage (proteolytic processing of the aminoterminal end of the CSP by a parasite cysteine protease) occurs following the initial binding of the aminoterminal RI+ region to the liver cell. Heparin sulfate proteoglycans on the hepatocytes trigger the protease which opens up the CSP protein (3) so that the high affinity binding between RIII+ and the liver cell can occur, which is the last step before penetration of the liver cell by the sporozoite.

5. Applicant is proposing to target the antibody and cellular immune response to the RIII+(or TSR) region of the CSP. Selection of the fragment from the RHI+ region for attachment to the aminoterminal end of the ecdCD40L, will be based on a size of the antigen fragment chosen should be such so as to be small enough so that it does not disrupt assembly of the CD40L homotrimer, and the presence of the heparin sulfate binding regions, and epitopes that bind to Class I and II MHC.

6. Moreover, inducing an immune response simultaneously to three separate epitopes reduces the probability that a single or even two point mutations in the malaria parasite can enable the parasite to escape the immune response induced by the vaccination.

Final Formulation of the Vaccine.

There are three adenoviral expression vectors for this composition/vaccine:

1. The composition/vaccine will be an adenoviral expression vector encoding the epitope of the aminotermus of the CSP (Region RI+) which binds with low affinity to the heparin sulfate proteoglycans on the hepatic cells attached to the aminoterminal end of the ecdCD40L. This vaccine is called: Ad-sig-CSPNterRg1/ecdCD40L.

2. The composition/vaccine will be an adenoviral expression vector encoding sequences from Region RII+ of CSP attached to the aminoterminus of the CD40L. This is a region of the CSP in which the amino acid sequences have been shown to be stable among many isolates. This composition/vaccine is called the Ad-sig-CSPRg2/ecdCD40L vaccine.

3. The composition/vaccine will be an adenoviral expression vector encoding the TSR region of the carboxytermus of the CSP (Region RIII+), which is a protein important in the high affinitiy binding and entry of the sporozoite into the hepatic cells attached to the ecdCD40L. This composition/vaccine is named: Ad-sig-CSFTSR/ecdCD40L.

The preferred strategy is to administer a mixture of expression vectors in which each vector encodes a ecdCD40L attached to a different fragment or region of the CSP. An alternative strategy which is possible consists of the three fragments of the CSP protein (see above) attached in tandem array and where the 3 fragment peptide is attached to the ecdCD40L constituting a chimeric fusion protein.

Mode of Administration.

The composition/vaccine is a mixture of three adenoviral expression vectors which will be given SC every week for three successive weeks. As stated above, an alternative strategy is to create a transcription unit in a single expression vector which encodes the three fragments of CSP connected together in tandem array which is then attached to a linker which in turn is attached to the amino terminal end of the ecdCD40L.

The general criteria utilized for selecting fragments of the CSP protein, which when attached to the aminoterminal end of the ecdCD40L, can generate both a cellular and neutralizing antibody immune response are as follows:

1. To prevent a malarial infection by generating high levels of CSP protein specific neutralizing antibodies to malaria, the fragment must have the ability to be recognized and bound by Class II MHC and occupy a region in CSP needed for infection of cells by malaria;

2. To suppress a malarial infection already established by generating high levels of CSP protein specific CD8 effector T cells, the fragment must be recognized by and bound by Class I MHC and capable of appearing on the surface of infected cells once infection has been established;

3. To prevent or reduce the probability of escape from the negative selective pressure of the immunological response due to sequence evolution of regions of the CSP protein selected for the vaccine by attaching 2 or more fragments of the CSP protein in tandem to the aminoterminal end of the ecdCD40L;

4. To prevent the destabilization of the homotrimeric structure of the ecdCD40L from the attachment of the TAA to the aminoterminal end of the ecdCD40L, the fragments of the CSP protein will be chosen such that the molecular weight of the combined TAA is not too large.

The choice of the fragments from the CSP protein is further refined by using a method for identifying fragments which find non-cross reacting neutralizing antibodies, which are from regions of the CSP protein which are associated with different functions of the CSP protein.

This method involves the following steps:

1. Isolation of neutralizing antibodies to the malarial CSP protein,

2. Identification of non-cross reacting neutralizing antibodies by mapping the binding of these malarial neutralizing to different regions of the CSP protein, 3. Characterization of the physical properties of the fragments of the CSP protein which bind non-cross reacting neutralizing antibodies. Examples of physical properties are as follows: hydrophobicity, acidic or basic net charge, amino acids with sulfhydryl groups or glycosylation sites, presence of an alpha helical regions or beta pleated sheet regions. Fragments which bind non-cross reacting neutralizing antibodies which have difference with respect to the presence or absence of such physical properties are assumed to be highly likely belonging to regions of the CSP protein which have different functions which are listed above.

4. The goal is to create a multi-fragment vaccine which induces non-cross reacting neutralizing antibodies which block virulence functions of the malarial parasite.

The invention illustratively described herein suitably may be practiced in the absence of any element or elements, limitation or limitations which is not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. This, it should be understood that although the present invention has been specifically disclosed by preferred embodiments and optional features, modification and variation of the concepts herein disclosed may be restored to by those skilled in the art, and that such modifications and variations are considered to be within the scope of this invention as defined by the appended claims.

Other embodiments are set forth within the following claims.

Published Papers Relevant to the Malarial Sporozoite TAA/ecdCD40L Vaccine

1. World Health Organization. Twelfth program report of the UNDP/World Bank/WHO special program for research and training in tropical diseases. Bull World Health Organ 12: 64-76, (1995).

2. WHO: World malaria report. The WHO global malaria programme (2008).

3. Coppi A, Natarajan R, Pradel G, Rennett B L, James E R, Roggero M A, Corradin G, Persson C, Tewari R, and Sinnis P. The malaria circumsporozoite protein has two functional domains, each with distinct roles as sporozoites journey from mosquito to mammalian host. Journal of Experimental Medicine 208: 341-356, (2011).

4. Rowe J A, Claessens A, Corigan R A, and Arman M. Adheson of *P. falciparum*-infected erythrocytes to human cells: molecular mechanisms and therapeutic implications. Expert Reviews in Molecular Medicine, 11, e16doi: 10.1017/S1462399409001082.

5. Biswas A K, Hafiz A, Banerjee B, Kim K S, Daatta K, and Chitis C E. *Plasmodium falciparum* uses gClqR/HAB1/p32 as a receptor to bind to vascular endothelium and for platelet-mediated clumping. PLoS Pathog 3(9): e130. Doi:10.1371/j ournal.ppat.0030130.

6. Robinson B A, Weich T L and Smith J D. Widespread functional specialization of *Plasmodium falciparum* erythrocyte membrane protein' family members to bind CD36 analyzed across a parasite genome. Molecular Microbiology 47: 1265-12778, (2003).

7. Smith J D, Subramanian G, Gamain B, Baruch D I, and Miller L H. Classification of adhesive domains in the *Plasmodium falciparum* erythrocyte membrane protein family. Mol Brioche Parasitol 110: 293-310, (2000).

8. Barnwell J W, Asch A S, Nachman R L, Yamaya M, Alkaw M, and Ingravello P. A human 88-kD membrane glycoprotein CD36) functions in vitro as a receptor for a cytoadherence ligand on *Plasmodium falciparum*-infected erythrocytes. J Clin Invest 84: 765-772, (1989).

9. Siano J P, Grady K K, Millet P, and Wick T$_M$. Short Report: *Plasmodium falciparum*: cytoadherence to alpha v beta 3 on human microvascular endothelial cells. Am J Trop Hyg 59: 77-79, (1998).

10. McKormick C J, Craig A, Roberts D, Newbold C I, and Berendt A R. Intercellular Adhesion Molecule-1 and CD26 synergize to mediate adherence of *Plasmodium falciparum*-infected erythrocytes to cultured human microvascular endothelial cells. J Clin Invest 100: 2521-2529, (1997).

11. Blythe J E, Yam X Y, Kuss C, Bozdech Z, Holder A A, Marsh K, Langhorne J, and Preiser P R. Infect Immun 76: 3329.DOI:10.1128/IAI.01460-07.

12. Kyes S A, Rowe J A, Kriek N, and Newbold C I. Rifins: a second family of clonally variant proteins expressed on the surface of red cells infected with *Plasmodium falciparum*. Proc. Natl. Acad. Sci. USA. 96: 9333-9338, (1999).

13. Schuldt N J, Aldhamen Y A, Appledorn D M, Seregin S S, Kousa Y et al, 20111). Vaccine platforms combining circumsporozoite protein and potent immune modulators, Rea or EAT-2, paradoxically result in opposing immune responses. PLoS ONE 6(8): e24147.doi:10.1371/journal.pone.024147.

14. Singh A P, Buscaglia C A, Wang Q, Levay A, Nussenzweig D R, Walker J R, Winzeler E A, Fujii H, Fontoura R M, and Nussenzweig V. *Plasmodium* circumsporozoite protein promotes the development of the liver stages of the parasite. Cell 131: 492-504, (2007).

15. Overstreet M G, Cockburn I A, Chen Y C, and Zavala F. Protective CD8+ T cells against *Plasmodium* liver stages: immunobiology of an 'unnatural' immune response. Immunological Reviews 225: 272-283, (2008).
16. Roberts D J, Craig A G, Berendt A R, Pinches R, Nash G, Marsh K, and Newbold C I. Rapid switching to multiple antigenic and adhesive phenotypes in malaria. Nature 357: 689-692, (1992).
17. Kaesti J, Cockburn I A, Cortes A, Baea K, Rowe J A, and Beck H P. Virulence of malaria is associated with differential expression of *Plasmodium falciparum* var gene subgroups in a case-control study. Journal of Infectious Diseases 193: 1567-1574, (2006).
18. Nussenzweigh et al in Nature 341: 323-326, (1989)
19. Kumar K A, Sano G I, Boscardin S, Nussenzweig R S, Nussenzweig M C, Zavala F and Nussenzweig V. The circumsorozoite protein is an immunnodominant protective antigen in irradiated sporozoites. Nature 444: 937-940, (2006).
20. Lalvani A, Moris P, Voss G, Pathan A A, Kester K E, Brookes R, Lee E, Koutsoukos M, Plebanski M, Delchambre M, Flanagan K L, Carton C, Slaoui M, Van Hoecke C, Ballou W R, Hill A V S, and Cohen J. Potent induction of focused Th1-Type cellular ad humoral immune responses by RTS,S/SBAS2, a recombinant *Plasmodium falciparum* malaria vaccine. Journal of Infectious Diseases 180: 1656-1664, (1999).
21. Gordon D M, McGovern T W, Krzych U et al. Safety, immunogenicity and efficacy of a recombinantly produced *Plasmodiium falciparum* circumsporozoite protein hepaptitis B surface antigen subunit subunit vaccine. J. Infect. Dis. 171: 15761585, (1995).
22. Plassmeyer M L, Reiter K, Shimp, Jr. R, Kotova S, Smith P D, Hurt D E, House B, Zou X Y, Zhang Y L, Hickman M, Uchime O, Herrera R, Nguyen V, Glen J, Lebowitz J, Jin A J, Miller L G, MacDonald N J, Wu Y, and Narum D L. Structure of the *Plasmodium falciparum* circumsporozoite protein, a leading malaria vaccine candidate. J Biol Chem 284: 26951-26963, (2009).
23. Gregson A L, Oliveira G, Othoro C, Calvo-Calle J M, Thorton G B, Nardin E, and Edelman R. Phase I trial of an alhydrogel adjuvanted hepatitis B core virus-like particle containing epitomes of *Plasmodium falciparum* circumsporozoite protein. PLos ONE 3(2): e1556.doi.10.1371/journal.pone.0001556.
24. Asante K P, Abdulla S, Agnandji S, Kyimo J, Vekemans J et al. Safety and efficacy of the RTS,S/AS01E candidate malaria vaccine given with expanded-programme-on-immunisation vaccines: 19 month follow-up of a randomised, open-label, phase 2 trial. Lancet Infect Dis 11: 741-749, (2011).
25. Kester K E, Cummings J F, Ockenhouse C F, Nielsen R, Hall B T, Gordon D M, Schwenk R J, Krzych U, Holland C A, Richmond G, Dowler M G, Williams J, Wirtz R A, Tomieporth N Vigneron L, Delchambre M, Demoitie M A, Ballou W R, Cohen J, Hener D G Jr. Phase 2a trial of 1, 2, and 3 month and 1, 7, and 28 immunization schedules of malaria vaccine RTS,S/AS02 in malaria-naïve adults at the Walter Reed Army Institute of Research. Vaccine 26: 2191-2202, (2008).
26. The RTS, S Clinical Trials Partnership. First results of phase 3 trial of RTSS/AS01 malaria vaccine in African children. NEJM365: 1863-1875, (2011).
27. The RTS,S Clinical Trials Partnership. A phase 3 trial of RTS,S/AS01 malaria vaccine in African infants. Published on line (Nov. 9, 2012) in the New England Journal of Medicine, DOI: 1056/NEJMoa1208394.
28. Jefferson T et al. Efficacy and effect of influenza vaccines in the elderly. Lancet 264: 1165-1174, (2005).
29. Goodwin K, Vibou C, Simonsen L. Antibody response to influenza vaccination in the elderly: a quantitative review. Vaccine 24: 1159-1169, (2006).
30. Jackson M L, Nelson J C, Weiss N S et al. Influenza vaccination and risk of community acquired pneumonia in immunocompetent elderly people: a population based nested case control study. The Lancet 372: 398-405, (2008).
31. Simonsen L, Taylor R J. Mortality benefits of influenza vaccination in elderly people: an ongoing controversy. Lancet Infect Dis 7: 658-666, 2007, Kraus A A, Haymore L B et al. Dengue virus neutralization by human immune sera: role of envelope protein domain III-reactive antibody. Virology 392: 103-113, (2009).
32. Dong L, More I, Hossain J M, Liu B, and Kimjra Y. An immunostimulatory oligodeoxynucleotide containing a cytosine-guanosine motif protects senescence-accelerated mice from lethal influenza virus by augmenting the T helper type 1 response. Journal of General Virology 84: 1623-1628, 2003.
33. Eaton S M, Burns E M, Kusser K, Radall T D, and Haynes L. Age-related defects in CD4 T cell cognate helper function lead to reductions in humoral responses. J Exp Med 200: 1613-1622, 2004.
34. Zhang, L, Tang, Y, Akbulut H, Zelterman D, Linton P-J, and Deisseroth, A. An adenoviral vector cancer vaccine that delivers a tumor-associated antigen/CD40-ligand fusion protein to dendritic cells. PNAS, 100: 15101-15106, (2003).
35. Akbulut, H, Tang, Y, Maynard J, Zhang L, Pizzorno G, and Deisseroth, A. Vector targeting makes 5-fluorouracil chemotherapy less toxic and more effective in animal models of epithelial neoplasms. Clin Cancer Res 10: 7738-7746, (2004).
36. Tang, Y, Zhang, L, Yuan, J, Akbulut H, Maynard J, Linton P-J, and Deisseroth, A. Multistep process through which adenoviral vector vaccine overcomes anergy to tumor-associated antigens. Blood, 104: 2704-2713, (2004).
37. Akbulut H, Tang Y C, Akbulut K G, Maynard J, Zhang L, Deisseroth A. Antitumor immune response induced by i.t. injection of vector activated dendritic cells and chemotherapy suppresses metastatic breast cancer. Mol Cancer Ther 5:1975-1985, (2006).
38. Tang Y C, Maynard J, Akbulut H, Fang X M, Zhang W W, Xia X Q, Koziol J, Linton P-J, and Deisseroth A. Vaccine which overcomes defects acquired during aging and cancer. Journal of Immunology 177:5697-5707, (2006).
39. Tang Y, Akbulut H, Maynard J, Zhang L, Petersen L, and Deisseroth A. Vaccine strategies for cancer and infectious diseases in the elderly. Gene Therapy, Eds. Takenori Ochiai, Hideaki Shimada, and Masatoshi Tagawa, Published by Japanese Ministry of Education and Science, pp. 78-85, (2007).
40. Akbulut H, Akbulut K G, Tang Y C, Maynard J and Deisseroth A. Chemotherapy targeted to cancer tissue potentiates antigen specific immune response induced by vaccine for In vivo antigen loading and activation of dendritic cells. Molecular Therapy, 10:1753-1760, (2008).
41. Tang, Y C, Linton, P J, Thoman M, and Deisseroth A. Symposium in Writing: Vaccine for infections and cancer. Cancer Immunology and Immunotherapy, 58: 1949-1957, (2009).

42. Han T H, Tang, Y C, Park Y H, Petersen L, Maynard J, Li P C, and Deisseroth A. Ad-sig-BcrAbl/ecdCD40L vector prime-BcrAbl/ecdCD40L protein boost vaccine for P210Bcr-Abl protein. Bone Marrow Transplantation, (2009).
43. Akbulut H, Tang Y, Akbulut K G, Maynard J, and Deisseroth A. Addition of adenoviral vector targeting of chemotherapy to the MUC-1/ecdCD40L VPPP vector prime protein boost vaccine prolongs survival of mice carrying growing subcutaneous deposits of Lewis lung cancer cells. Gene Therapy, 17: 1333-1340, (2010).
44. Deisseroth A, Tang Y, Zhang L, Akbulut H, and Habib N. TAA/ecdCD40L adenoviral prime-protein boost vaccine for cancer and infectious disease. Cancer Gene Therapy 20: 65-69, 2013.
45. Ancsin J B, and Kisilevsky R. A binding site for highly sulfated heparan sulfate is identified in the N-terminus of the circumsorozoite protein. J Biol Chem 279: 21824-21832, (2004).
46. Ying P, Shakibaei M, Patankar M S, Clavijo P, Beavis R C, Clark G F, and Frevert U. The malaria circumsporosoite protein: interaction of the conserved regions RI+ and RII+ with heparin like oligosaccharides. Experimental Parasitology 85: 168-182, (1997).
47. Cerami C, Frevert U, Sinnis P, Takacs B, Clavijo P, Santos M, and Nussenzweig V. The basolateral domain of the hepatocyte plasma membrane bears receptors for the circumsporozoite protein of P. falciparum sporozoites. Cell 70: 1021-1033, (1992).
48. Wengelnik K, Spaccapelo R, Naitza S, Robson K J H, Janse C H, Bistoni F, Waters A P, and Crisanti A. The A-domain and the thrombospondin-related motif of P falciparum TRAP are implicated in the invasion process of mosquito salivary glands. EMBO Journal 18: 5195-5204, (1999).
49. Doud M B, Koksal A C, Mi L Z, Song G, Lu C, and Springer T A. Unexpected fold in the circumsporozoite protein target of malaria vaccines. Proc. Natl. Acad. Sci, USA, accepted Apr. 4, 2012.
50. Mongui A, Angel D I, Moreno-Perez D A, Villarreal-Gonzalez S, Almonacid H, Vaegas M, and Patarroyo M A. Identification and characterization of the P. vivax thrombospondin-related apical merozoite protein. Malarial Journal 9: 283-291, (2010).
51. Plassmeyer M L, Reiter K, Simp, Jr R L, Kotova S, Smith P D, Hurt D E, Hoiuse B, Zou X, Zhang Y, Hickman M, Uchime O, Herrera R, Nguyen V, Glen J, Lebowitz J, Jin A J, Miller L H, MacDonald N, Wu Y, and Narum D L. Structure of the P. falciparum circumsporozoite protein, a leading malaria vaccine candidate. J. Biol. Chem. 284: 26951-26963, (2009).
52. Rathore D, Sacci J B, de la Vega P, and McCutchan T F. Binding and invasion of liver cells by P. falciparum sporozoites. J Biol Chem 277: 7092-7098, (2002).
53. Good M F, Maloy W L, Lunde M N, Margalit H, Cornette J L, Smith G L, Moss B, Miller L H, and Berzofsky J A. Construction of synthetic immunogen: use of new T-helper epitope on malaria circumsporozoite protein. Science 235:1059-1062, (1987).

The invention claimed is:

1. An immunogenic composition for generating an immune response in an individual against the malarial parasite comprising:
   an effective amount of a TAA/ecdCD40L (target associated antigen/extracellular domain of the CD40 ligand protein) composition comprising at least three different expression vectors, each expression vector comprising a transcription unit encoding a secretable fusion protein, wherein the secretable fusion protein comprises:
   (i) a secretory signal sequence for directing secretion of each fusion protein,
   (ii) one each of at least three epitopes, where each of said three epitopes comprises a fragment from a different one of three distinct regional locations respectively designated as the RI+, RII+, and TSR regions, of the CSP (Circumsporozoite protein) of said malarial parasite, and
   (iii) an ecdCD40L, where each of said three epitopes is linked to the amino terminal end of the ecdCD40 ligand,
   (iv) said three expression vectors collectively defining a multi-epitope TAA/ecdCD40L fusion immunogenic composition, wherein each of the TAA/ecdCD40L induces neutralizing antibodies which block functions of the CSP.

2. An immunogenic composition of claim 1, wherein said expression vectors are plasmids.

3. An immunogenic composition of claim 1, wherein each of said epitopes is selected to be small enough so that it does not disrupt assembly of a CD40L homotrimer.

4. An immunogenic composition of claim 1, wherein said expression vectors are adenoviral expression vectors.

5. An immunogenic composition of claim 1, wherein each of said epitopes of the malarial CSP is capable when linked to ecdCD40L to induce CD8 effector T cells and neutralizing antibodies.

6. An immunogenic composition of claim 5, wherein said neutralizing antibodies are non-cross reacting neutralizing antibodies, so that when the composition is administered, the composition has the ability to interrupt and block functions of the CSP which relate to the binding and penetration of an individual's liver cells by the malarial parasite.

7. An immunogenic composition of claim 1, wherein said epitopes are respectively, SEQ ID NOS 1, 2, and 3.

8. An immunogenic composition for generating an immune response in an individual against the malarial parasite comprising:
   an effective amount of a TAA/ecdCD40L (target associated antigen/extracellular domain of the CD40 ligand protein) composition comprising an expression vector comprising a transcription unit encoding a secretable fusion protein, wherein the secretable fusion protein comprises:
   (i) a secretory signal sequence for directing secretion of each fusion protein,
   (ii) at least three epitopes, where each of said three epitopes comprises a fragment from a different one of three distinct regional locations respectively designated as the RI+, RII+, and TSR regions, of the CSP (Circumsporozoite protein) of said malarial parasite, and
   (iii) an ecdCD40L, where said three epitopes are linked to each other and linked to the amino terminal end of the ecdCD40 ligand to define a TAA/ecdCD40L fusion immunogenic composition, wherein the TAA/ecdCD40L induces neutralizing antibodies which block functions of the CSP.

9. An immunogenic composition of claim 8, wherein said epitopes are respectively, SEQ ID NOS 1, 2, and 3.

10. A method for generating an immune response in an individual against a malarial parasite, using the immunogenic composition of claim 8.

11. A method for generating an immune response in an individual against a malarial parasite, using the immunogenic composition of claim 1.

* * * * *

SEQUENCE LISTING

```
<160> NUMBER OF SEQ ID NOS: 3

<210> SEQ ID NO 1
<211> LENGTH: 20
<212> TYPE: PRT
<213> ORGANISM: Artificial Sequence
<220> FEATURE:
<223> OTHER INFORMATION: Synthetic Construct

<400> SEQUENCE: 1

Gly Asn Asn Glu Asp Asn Glu Lys Leu Arg Lys Pro Lys His Lys Lys
1               5                   10                  15

Leu Lys Gln Pro
            20

<210> SEQ ID NO 2
<211> LENGTH: 27
<212> TYPE: PRT
<213> ORGANISM: Artificial Sequence
<220> FEATURE:
<223> OTHER INFORMATION: Synthetic Construct

<400> SEQUENCE: 2

Thr Glu Trp Ser Pro Cys Ser Val Thr Cys Gly Asn Gly Ile Gln Val
1               5                   10                  15

Arg Ile Lys Pro Gly Ser Ala Asn Lys Pro Lys
            20                  25

<210> SEQ ID NO 3
<211> LENGTH: 23
<212> TYPE: PRT
<213> ORGANISM: Artificial Sequence
<220> FEATURE:
<223> OTHER INFORMATION: Synthetic Construct
```

```
<400> SEQUENCE: 3

Trp Asp Glu Trp Ser Pro Cys Ser Val Thr Cys Gly Lys Gly Thr Arg
1               5                   10                  15

Ser Arg Lys Arg Glu Ile Leu
            20
```